(12) United States Patent
John et al.

(10) Patent No.: US 10,258,072 B2
(45) Date of Patent: Apr. 16, 2019

(54) ENVIRONMENTALLY FRIENDLY GELATOR USING MEDIUM CHAIN TRIGLYCERIDES AND METHOD OF USE

(71) Applicant: Research Foundation of the City University of New York, New York, NY (US)

(72) Inventors: George John, New York, NY (US); Julian Silverman, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 147 days.

(21) Appl. No.: 15/526,561

(22) PCT Filed: Nov. 12, 2015

(86) PCT No.: PCT/US2015/060336
§ 371 (c)(1),
(2) Date: May 12, 2017

(87) PCT Pub. No.: WO2016/077556
PCT Pub. Date: May 19, 2016

(65) Prior Publication Data
US 2017/0311639 A1    Nov. 2, 2017

Related U.S. Application Data

(60) Provisional application No. 62/078,605, filed on Nov. 12, 2014.

(51) Int. Cl.
*A23L 29/20*    (2016.01)
*C07H 13/06*    (2006.01)
(Continued)

(52) U.S. Cl.
CPC ............. *A23L 29/206* (2016.08); *A23L 29/20* (2016.08); *C07H 7/02* (2013.01); *C07H 13/06* (2013.01);
(Continued)

(58) Field of Classification Search
CPC ........ C07H 13/06; A23L 29/20; A23L 29/206
See application file for complete search history.

(56) References Cited

U.S. PATENT DOCUMENTS 2,492,173 A    12/1949 Mysels
5,892,116 A    4/1999 Weiss et al.
(Continued)

FOREIGN PATENT DOCUMENTS

JP    2000290177    10/2000
WO    WO2010033726    3/2010
(Continued)

OTHER PUBLICATIONS

Balachandran, V. et al.; Adhesive Vesicles through Adaptive Response of a Biobased Surfactant; Angewandte Chemie; 2010; pp. 9699-9702; 122; Wiley-VCH Verlag GmbH & Co. KGaA, Weinheim.
(Continued)

*Primary Examiner* — Michele L Jacobson
*Assistant Examiner* — Changqing Li
(74) *Attorney, Agent, or Firm* — Peter J. Mikesell; Schmeiser, Olsen & Watts, LLP

(57) ABSTRACT

A gel is disclosed that is formed from a hydrophobic liquid and a gelator. The gelator has a structure given by: formula (I) where (II) and (III) or (IV) or (V). The gelator is environmentally friendly and from a biomass source.
(Continued)

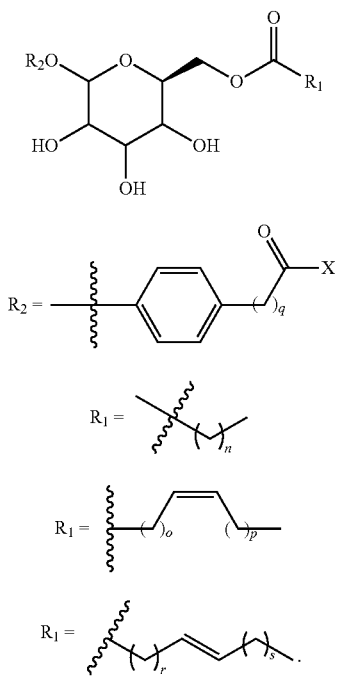

(51) Int. Cl.
| | |
|---|---|
| *A23L 29/206* | (2016.01) |
| *C07H 7/02* | (2006.01) |
| *C07H 13/00* | (2006.01) |
| *A61K 47/32* | (2006.01) |
| *A61K 47/34* | (2017.01) |
| *A23L 29/288* | (2016.01) |

(52) U.S. Cl.
CPC .............. *A23L 29/288* (2016.08); *A61K 47/32* (2013.01); *A61K 47/34* (2013.01); *C07H 13/00* (2013.01)

(56) References Cited

U.S. PATENT DOCUMENTS

| | | |
|---|---|---|
| 8,318,178 B2 | 11/2012 | Majmudar |
| 2008/0050434 A1 | 2/2008 | Jain et al. |
| 2012/0258059 A1 | 10/2012 | Iwama et al. |

FOREIGN PATENT DOCUMENTS

| | | | |
|---|---|---|---|
| WO | WO-2010033726 A2 * | 3/2010 | ............... A61K 9/06 |
| WO | WO2010143066 | 12/2010 | |

OTHER PUBLICATIONS

Gumel, A.M.; Lipase mediated synthesis of sugar fatty acid esters; Process Biochemistry; Aug. 4, 2011; pp. 2079-2090; (46); Elsevier.
Jadhav, S. et al.; Medium-Chain Sugar Amphiphiles: A New Family of Healthy Vegetable Oil Structuring Agents; J. Agric. Food Chem.; Nov. 15, 2013; pp. 12005-12011; (61); ACS Publications.
Sawalha, H. et al.; Organogel-Emulsions with Mixtures of β-Sitosterol and γ-Oryzanol: Influence of Water Activity and Type of Oil Phase on Gelling Capability; J. Agric. Food Chem.; Mar. 7, 2012; pp. 3462-3470; (60); ACS Publications.
Co, E. et al.; Organogels: An Alternative Edible Oil-Structuring Method; J Am Oil Chem Soc; Mar. 29, 2012; pp. 749-780; (89); Springer.
Vidyasagar, A. et al.; Soft Optical Devices from Self-Healing Gels Formed by Oil and Sugar-Based Organogelators; Angew. Chem. Int. Ed.; 2011; pp. 8021-8024; (50) ; Wiley-VCH Verlag GmbH & Co. KGaA, Weinheim.
ISA/US), International Search Report (ISR) from PCT Application No. PCT/US2015/060336 dated Feb. 2, 2016 (total 9 pages).
John, G. et al. Biorefinery: A Design Tool for Molecular Gelators; Langmuir; May 13, 2010; pp. 17843-17851; 26(23); American Chemical Society.
Abdallah, D. et al.; Organogels and Low Molecular Mass Organic Gelators; Advanced Materials; Sep. 1, 2000; pp. 1237-1247; vol. 12, No. 17; Wiley-VCH Verlag GmbH, D-69469 Weinheim.
Jadhav, Swapnil, Chapter 1: Introduction to Molecular Gels, Thesis, City University of New York; 2012.

* cited by examiner

20 Claims, 6 Drawing Sheets

ENVIRONMENTALLY FRIENDLY GELATOR USING MEDIUM CHAIN TRIGLYCERIDES AND METHOD OF USE

CROSS-REFERENCE TO RELATED APPLICATIONS

This application claims priority to and is a non-provisional of U.S. Patent Application Ser. No. 62/078,605 (filed Nov. 12, 2014) the entirety of which is incorporated herein by reference.

BACKGROUND OF THE INVENTION

The subject matter disclosed herein relates to gel comprising environmentally friendly gelators and method of producing such gels. The recent ban of trans-fats and evolving discussion on the safety of saturated fats has opened the floor to healthful oils and novel oil structuring agents. Medium-chain ($C_8$-$C_{12}$) triglyceride fats and oils have been demonstrated as viable potential alternatives to long-chain fatty acyl oils in creating functional gels and composites for food, medical and personal care applications. As edible, personal care, and cosmetic oil mixtures depend greatly on the nature of the oil for their organoleptic, rheological, and functional properties, exploring applications of medium-chain triglyceride (MCT) oils may result in viable value-added formulations.

Towards the development of small molecule solutions to replace unhealthy trans-fat structuring agents, edible oil gels, known as oleogels, have piqued researcher's interests by modifying formulation rheology with low molecular weight gelators, or more simply, molecular gelators (MGs). While natural and synthetic polymers, mostly methylated and ethylated cellulose derivatives, have been demonstrated as viable oil structuring agents, the serendipitous discovery of small molecule self-assembly as a method for structuring solvents has lead to the development and study of numerous MGs. From gelator design to network assembly and characterization, the variety of self-assembled networks of MGs demonstrates an interdisciplinary effort to design functional MG systems for a myriad of solvents and liquid mixtures. Despite the popularity and functionality of MCT fats and oils, there are relatively few efforts focused on developing MGs to specifically gel this increasingly popular category of oils.

The discussion above is merely provided for general background information and is not intended to be used as an aid in determining the scope of the claimed subject matter.

BRIEF DESCRIPTION OF THE INVENTION

This work comprises the synthesis and gelation of a small molecule system capable of gelating edible and inedible organic solvents. The gelator is made from environmentally friendly biologically based components, and forms robust crystalline fibers in solution, which grow to entrap the liquids forming a spongy gel. These gels are importantly thixotropic and may be easily spread and allowed to re-thicken. They may be applied to food, fuel, and cosmetic application where oils are used.

In a first embodiment, a gel is provided. The gel comprises a hydrophobic liquid that has been formed into a gel through the addition of a composition having a structure given by

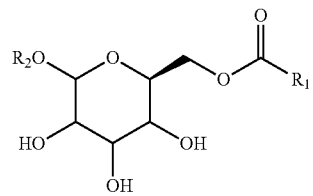

wherein

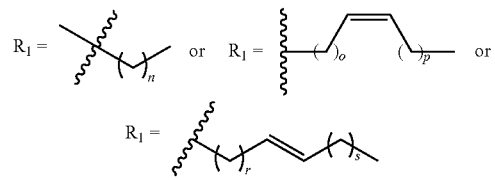

where n is an integer between 4 and 20; r and s are integers between 0 and 20 that sum to a digit between 4 and 20 and o and p are integers between 0 and 20 that sum to a number between 4 and 20;

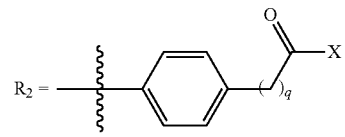

where q is an integer between 1 and 5 and X is a methyl, a hydroxyl or an ester.

In a second embodiment, a gel is provided. The gel comprises a hydrophobic liquid that has been formed into a gel through the addition of a composition having a structure given by:

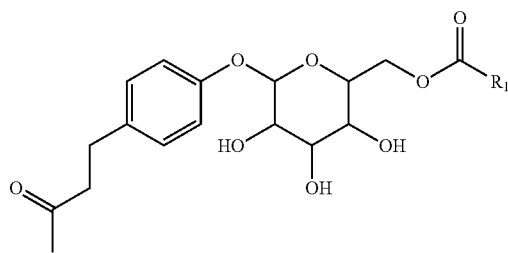

wherein

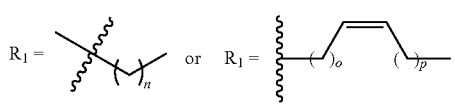

where n is an integer between 4 and 20 and o and p are integers that sum to a number between 4 and 20.

In a third embodiment a method for forming a gel is provided. The method comprises steps of exposing a hydrophobic liquid to a composition having a structure given by:

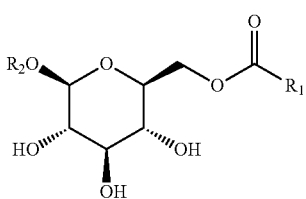

wherein

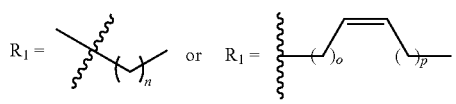

where n is an integer between 4 and 20 and o and p are integers that sum to a number between 4 and 20; $R_2$ is

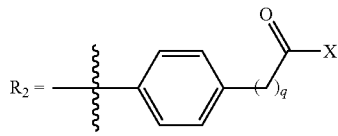

where q is an integer between 1 and 5 and X is a methyl, a hydroxyl or an ester; and permitting the hydrophobic liquid to thicken to form a gel.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
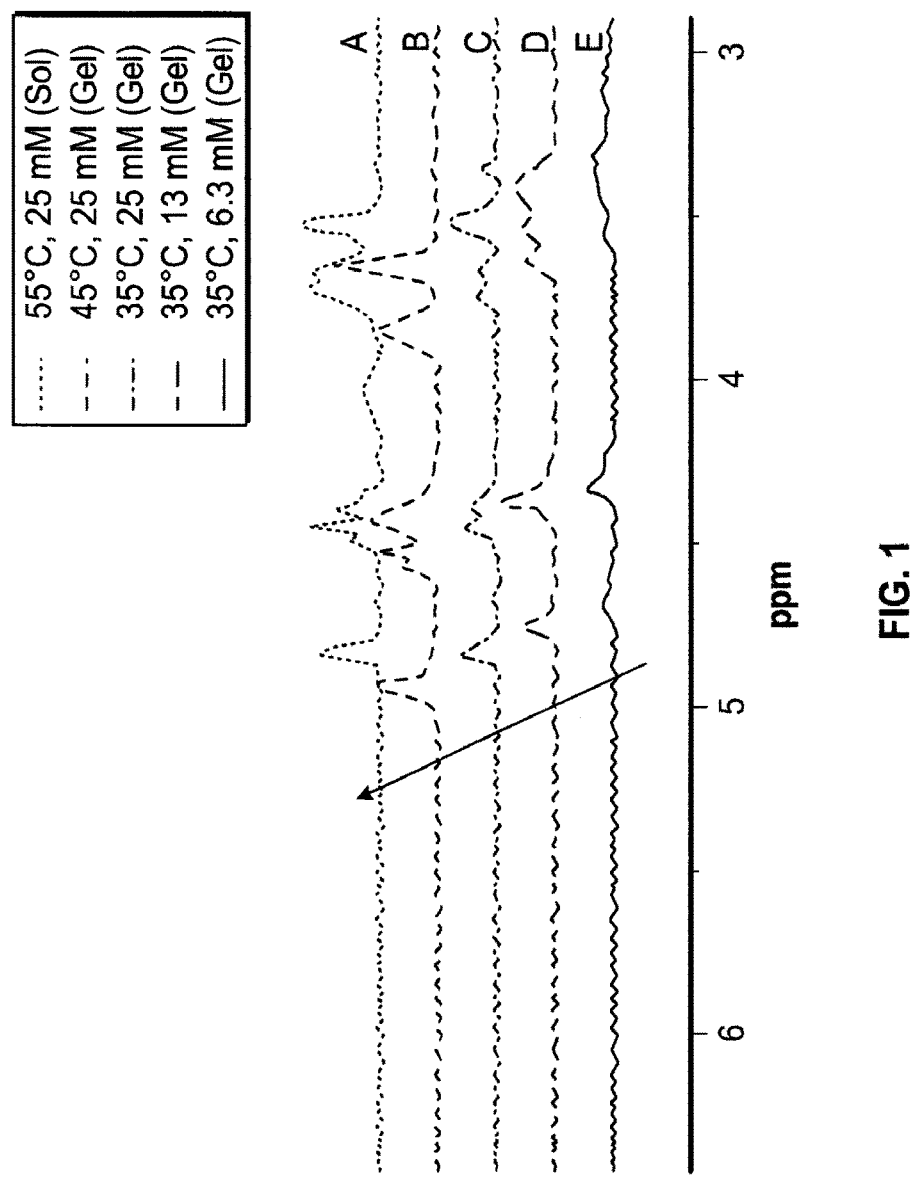
FIG. 1 is a 1H NMR spectra of RKG8 mixtures in toluene showing a close up on the shifting carbohydrate peaks wherein (a) is the solution and (b-e) are in the gel state depicting shifting in the pyranose hydrogen at the C1 position at about 2.9 ppm following stretched hydrogen bond in the gel that then relaxes when the molecules are in solution.

This disclosure provides a versatile organogelator from biobased reagents. By exploiting a relatively unexplored class of solvents, MCT oils, these gelators may be used in next-generation formulations for multifunctional materials. As the structure serves to structure oils in a fat mimicking fashion, they are a viable edible oil structuring agents for a host of applications. Novel small molecule sugar ester gelators were synthesized using biocatalysis for use as sustainable value-added materials from biomass. The facile one-step regiospecific coupling of a pro-antioxidant raspberry ketone glucoside and unsaturated or saturated long- and medium-chain fatty acids provides a simple approach to tailor the structure, and self-assembly of the amphiphilic product. These low molecular weight molecules demonstrated the ability to self-assemble in a variety of solvents and exhibited supergelation (MGC: less than 0.25 wt. %) in a range of natural edible oils as well as numerous organic solvents. Due to their ability to structure and gel a host of aprotic solvents, the gelators were characterized and tested in formulations with relatively unstudied solvents: natural medium-chain triglyceride oils, specifically coconut oil. By matching the gelators with functional medium-chain triglyceride oils to develop multifunctional formulations of stable clear oleogels, one can tailor desirable properties to afford next generation structured oils without the use of deleterious trans-fats. X-ray diffraction analysis indicates fatty acid chain packing of gelators is similar to that of natural fats, signifying the crystalline nature may lead to desirable textural properties and mouthfeel.

As more and more chemicals generally recognized as unsafe continue to be removed from consumer products, it is important that their replacements, the next generation of functional chemicals, serve to improve upon economic, and importantly, environmental costs. Developing soft functional materials from biomass serves not to limit the variety of chemical progress, but rather to use biomimesis as inspiration. Structured oils and fats, long at the forefront of the battle against trans-fats and in favor of healthy hearts, represent the continued need for research into soft matter. Furthermore, by studying natural products and their derivatives, research may serve to inform us on the chemistry of natural systems, and subsequently help serve to develop healthful eco-friendly alternatives to conventional rheology modifiers.

The pro-antioxidant raspberry ketone glucoside was coupled with saturated (caprylic and stearic) and unsaturated (oleic) fatty acid tails (Scheme 1). To explore the amphiphile's gelation capability, medium- and long-chain oils were mixed to form a variety of structured fats depending on the gelator concentration. The individual fatty acid, glucose, and phenol residue can be probed for further functionality, and their role in hierarchical 3D self-assembly to better understand the complex phenomenon that is self-assembled small molecule gelation.

Scheme 1: Example synthetic scheme

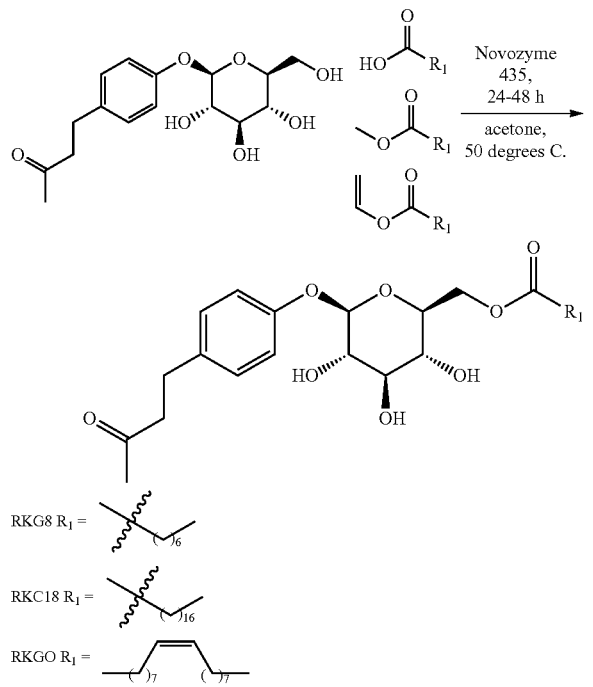

As disclosed in this specification, the versatility of the raspberry ketone glucoside derivatives to gelate a variety of aprotic liquids suggests small molecule gelation provides a powerful alternative to current oil processing methods. By programming functionality into bioderived surfactants, tailored formulations may be designed from the bottom up. Because consumer products exist as complex mixtures of raw materials, the exceedingly low concentration of gelator needed to solidify large quantities of oil, may serve to allow products to contain less filler, and more active ingredients.

The disclosed gelators may be used with a variety of MCTs. For example, a widely available MCT oil, coconut oil, is a major component of South and Southeast Asian diets, deriving antimicrobial, antifungal, and antiviral functionality from its constituent twelve-carbon lauric acid. Another versatile MCT oil, palm kernel oil, extracted from the edible seed of the oil palm tree, is often used after saponification in soap making due to its quick lathering, which is also attributed to its lauric acid content. By exploiting MCT derived fatty acids in mixtures as functional solvents for gels, MCT oleogels present as interesting multifunctional alternatives to conventional fat and oil mixtures. Further oils include hazel nut oil, grape seed oil, red palm oil and jojoba oil, olive oil, canola oil, soy oil, sunflower oil, and other edible triglycerides.

The gelators generally have a structure given by:

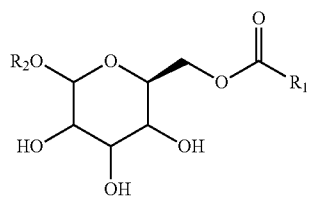

wherein

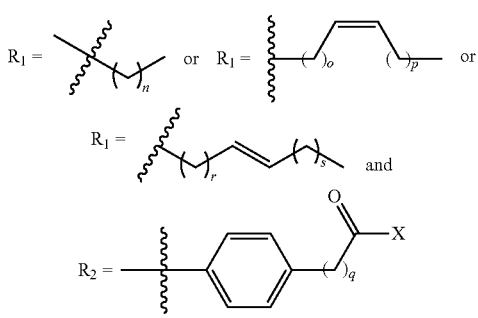

where n is an integer between 4 and 20; r and s are integers between 0 and 20 that sum to a digit between 4 and 20 and o and p are integers between 0 and 20 that sum to a number between 4 and 20; and q is an integer between 1 and 5 and X is a methyl, a hydroxyl or an ester. In another embodiment, n is between 5 and 9. In other embodiments n is 6 or 18. In another embodiment, n is between 15 and 20. In another embodiment, p and o sum to a number between 15 and 18. In another embodiment p and o are each 7. In another embodiment, the composition is present in the gel at a concentration of less than 2 g composition per 100 g of the organic solvent. Many sugars may be used including, for example, glucose, galactose, mannose and other monosaccharides. Examples of suitable organic solvents include hexanes, mineral oils, toluene, and ethers such as ethyl ether, etc.

Gelator Synthesis and Characterization. Two saturated fatty acid glucoside esters, raspberry ketone glucoside caprylate (RKG8) and raspberry ketone glucoside stearate (RKG18) were prepared via heterogeneous lipase-mediated esterification in non-aqueous media. Saturated caprylic and stearic acid, along with derivative methyl and vinyl esters were reacted with raspberry ketone glucoside in dried organic solvents. The monounsaturated raspberry ketone glucoside oleate (RKGO) was synthesized from vinyl oleate. The facile workup allows for simple catalyst regeneration, chromatographic solvent recycling, and monoacylated regiospecific product in high yields: 95% for caprylic acid vinyl ester reactions. The versatility and specificity of the Novozym 435 catalyst allows the synthesis of gelators with a wide range of hydrophobic-lipophobic balance values following a general biocatalytic coupling of reagents from renewable resources. To compare the compatibility of medium- and long-chain saturated fatty acid amphiphiles, gelator's MGC (Table 1), and melt temperatures (Table 2), were tabulated. To study the effect of unsaturation on self-assembly, the RKGO gels were compared to saturated analogues, though gelation of RKGO derivatives indicated a much higher MGC (greater than 0.5 vs. less than 0.5 wt. %). This lead the rheology and diffraction studies to focus on the robust saturated derivatives, specifically RKG8, due to exceedingly low MGC values.

TABLE 1

Gelation Index and Minimum Gelation Concentration Values

| Category | Solvent | Raspberry ketone glucoside | RKG8 | RKG18 | RKGO |
|---|---|---|---|---|---|
| Edible Oil | Hazelnut Oil | I | G (0.26) | G (0.24) | G (0.56) |
| Edible Oil | Coconut Oil | I | G (0.27) | G (0.28) | G (0.54) |
| Edible Oil | Grape seed Oil | I | G (0.25) | G (0.30) | G (0.66) |
| Edible Oil | Red Palm Oil | I | G (0.34) | G (0.36) | G (0.72) |
| Edible Oil | Jojoba Oil | I | G (0.25) | G (0.26) | G (0.48) |
| Organic Solvent | Hexanes | I | G (2.1) | G (0.24) | I |
| Organic Solvent | Mineral Oil | I | G (1.4) | G (0.24) | G (0.80) |
| Organic Solvent | Toluene | PS | G (0.5) | G (0.36) | G (0.73) |
| Aqueous Solvent | Water | PS | I | I | I |

I = Insoluble,
PS = Partially Soluble

TABLE 2

Temperature of Gelation values for gelators and gels

| Sample (Neat) | Melting Point (° C.) |
|---|---|
| RKG | 113-115 |
| RKG8 | 96-97 |
| RKG18 | 111-113 |
| RKGO | 96-98 |

| Sample (Gel) | $T_{gel}$ (° C.) |
|---|---|
| 5 wt. % RKG8 in Toluene | 48-50 |
| 5 wt. % RKG8 in Olive Oil | 108-110 |
| 5 wt. % RKG8 in Coconut Oil | 106-107 |
| 5 wt. % RKG18 in Coconut Oil | 111-112 |
| 5 wt. % RKGO in Coconut Oil | 105-109 |

As shown, many examples of molecular oil structurants exhibit dissimilar properties between bulk samples and the self-assembled structures. Characterizing the assembled intermolecular forces in the gelators is useful.

$^1$H NMR spectroscopy of the gelators in deuterated solvent revealed the disparate hydrogen environments between the alkyl (0.86-2.5 ppm), glucose (2.6-5.0 ppm), and phenolic hydrogen nuclei (about 7 ppm). See FIG. 1. As part of the planned structural design, these spatially distinct hydrogens serve to capitalize on their specific intermolecular interactions (van der Waals dispersive forces and hydrogen-bonding interactions). The role of hydrogen bonding interactions was probed by varying the concentration and temperature and following the shift of the glucose's hydrogen peaks. An increase in concentration or decrease in temperature shifted the secondary alcohol doublets in chloroform-d upfield, the former indicating the prevalence of intermolecular hydrogen bonding, which is desirable in developing a robust gelator. Similar shifts were seen in DMSO-d$_6$ by varying temperature, indicative of either inter- or intramolecular bonding. Interestingly, NMR spectra of gelled toluene were recorded, and similar shifts were observed, highlighting the importance of hydrogen bonding in the gelled medium. See FIG. 1. The peaks shift continually downfield until the sample reaches the gel-to-sol transition at about 49° C., at which point the peaks shift upfield with weaker hydrogen bonds.

Raspberry Ketone Glucoside Caprylate (((2R,3S,4S,5R,6S)-3,4,5-trihydroxy-6-(4-(3-oxobutyl)phenoxy)tetrahydro-2H-pyran-2-yl) methyl octanoate): FT-IR (neat) 3489 (m, $v$O—H), 3207 (b, $v$O—H), 2920 (m, sp$^3$ $v$C—H$_2$), 2850 (m, sp$^3$ $v$C—H$_2$), 1736 (s, ester $v$C=O), 1738 (s, ester $v$C=O), 1711 (s, ketone $v$C=O), 1512 (s, sp$^2$ Ar $\delta$C=C), 1230 (s, ester $v$C—O), 1009 (s, ether $v$C—O) cm-1. $^1$H NMR (CDCl$_3$, 300 MHz, 25° C.): δ 7.07 (d, 2H) 6.94 (d, 2H), 4.83 (d, 1H), 4.45 (d, 1H) 4.31 (d, 1H), 3.65 (s, 2H), 3.57 (s, 1H), 3.46 (s, 1H) 2.78 (d, 4H), 2.35 (t, 2H), 2.12 (s, 3H) 1.60 (t, 2H), 1.26 (s, 8H), 0.86 (s, 3H). $^{13}$C (CDCl$_3$, 300 MHz, 25° C.) 208.23 (ketone C=O), 173.38 (ester C=O), 156.21 (aryl), 135.20 (aryl), 130.68 (aryl), 128.60 (aryl), 117.83 (2C, aryl) 77.97 (gluc-C), 76.09 (gluc-C), 74.74 (gluc-C), 71.62 (gluc-C), 69.77 (gluc-C), 66.07 (gluc-CH$_2$), 45.08 (ketone α-CH$_2$), 36.04, 31.84, 29.08 (2C), 27.81, 25.14, 24.37, 22.74, 13.89 (fatty acid CH$_3$). MS (ESI) m/z (MH$^+$) 453.24, M.P.R. 96-97° C. Elem. Anal. Pred. C: 63.70, H: 8.02, Calc. C: 63.53, H: 8.02

Effect of Component Selection in Gel Preparation. The partial solubility of the glucoside gelator in oil solvents allows an invisible non-polar nanocrystalline network to form for a variety of oil solvents. Clear, semi-solid oleogels were formed by the dispersion of the derived gelators in oils up to exceedingly low nanomolar concentration (less than 0.25 wt. % m/v), comparable to other supergelators. Surprisingly, gelled samples of coconut and palm kernel oils are clear oleogels despite the opaque nature of the oil. The clarity of the coconut oleogels at 25° C. remained for up to and beyond one week, while palm kernel oil crystallized out in the gel samples forming an opaque gel within one hour of gel setting. The MGC of the caprylate gelator was determined by vial inversion to be 798 nM or 0.27 wt. %, comparable to the stearate derivative at 515 nM or 0.29 wt. % (Table 1). The oleate gelator exhibited similarly low, but higher MGC values in oils, indicating the cis-double bond does not preclude gelation capability at low concentrations. The comparable MGC values may be explained as the percolation threshold determining the minimum amount of gelator to bridge a specified domain, and represents the region of the phase diagram in which binary gelator solvent mixture to the sol phase. The melt temperature of the gels (T$_{gel}$) were similar between oils with varied triglyceride profiles, including a high percentage of monounsaturated oleic acid in olive oil, and medium-chain triglyceride coconut oil as demonstrated in Table 2. Palm kernel oil formulations could not be tested for MGC at room temperature, as the component oil is a solid fat. Comparable MGC and T$_{gel}$ values indicate the universal oleogel character of the solid gelator network that assembles in many types of edible oils, relatively independent of the fatty acid profile.

Figure 2A:
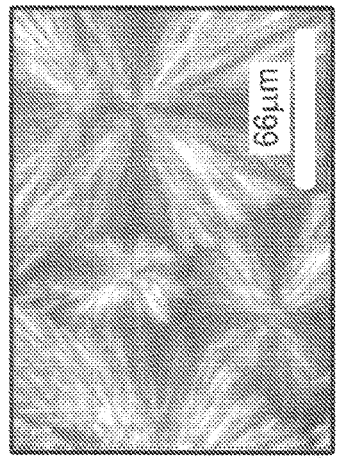
FIG. 2A to FIG. 2F are polarized optical microscopy images of neat coconut oil at 1 hour (FIG. 2A), coconut oil R8 gel crystals at 1 hour (FIG. 2B); coconut oil R8 gel crystals after 72 hours (FIG. 2C); scanning electron microscopy images of R8 xerogel (FIG. 2D) and the sample after extracting a coconut oil gel in hexanes (FIG. 2E) and an evaporated toluene organogel which displays sheet like ribbons of gelator fibers (FIG. 2F)
Figure 2B:
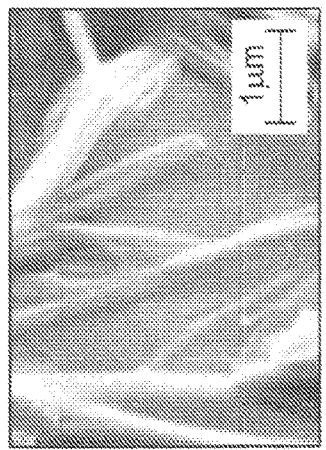
Figure 2C:
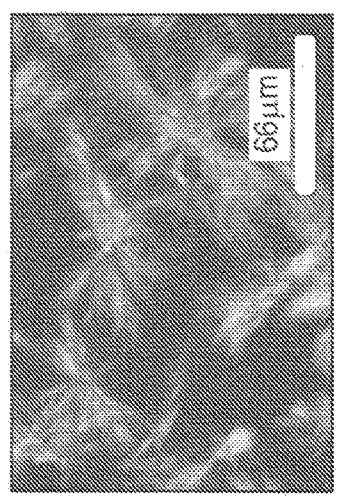
Figure 2D:
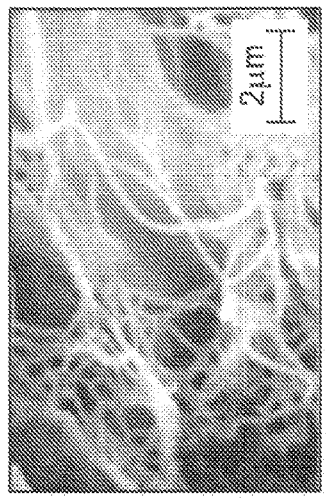
Figure 2E:
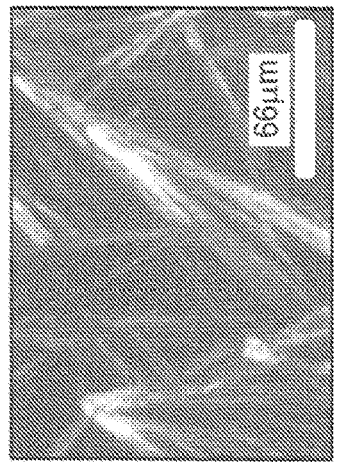
Figure 2F:
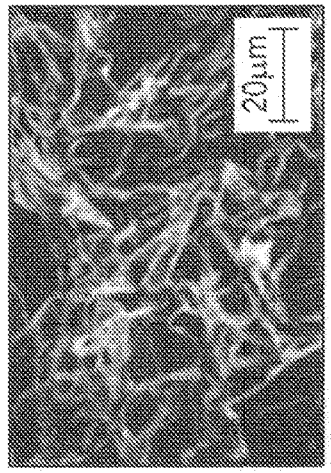

Polarized Optical and Scanning Electron Microscopy of Oleogels and Xerogels. Examining the gel samples under polarized light indicated the formation of birefringent networks (FIG. 2A-2C). Gels were prepared directly on slides to study the crystallization of coconut oil samples over time. Since a low temperature transition between an opaque and translucent gel phase (25-30° C.) corresponds to the crystallization of the medium-chain triglycerides (specifically the twelve-carbon lauric acid), it was evident that the RKG8, RKG18 and RKGO samples crystallized from a higher number of nucleation sites, compared to neat coconut oil, which melts between 24-32° C. Under 50× magnification, gel networks were still not visible, thus samples for electron microscopy were prepared by evaporating solvents from organogels and by extraction of the oil with solvent. FIG. 2D represents the gelator structure from a solvent evaporated sample exhibiting collapsed gel network. Solvent extracted fibers from oil demonstrate tubular shapes, while evaporated samples from toluene yields ribbon like fibers (FIGS. 2E and 2F). Both samples indicate the presence of fibrils, which comprise the vast network spanning and entrapping the solvent. FIG. 2A-2F: 2A) polarized optical microscopy images of neat coconut oil at 1 hour, 2B) coconut oil R8 gel crystals at 1 hour 2C) R8 coconut oil gel crystals after 72 hours. 2D) Scanning electron microscopy images of R8 xerogel. 2E) sample after extracting a coconut oil gel in hexanes: a close-up of the fibrous network and 2F) an evaporated toluene organogel which displays sheet like ribbons of gelator fibers.

Figure 3:
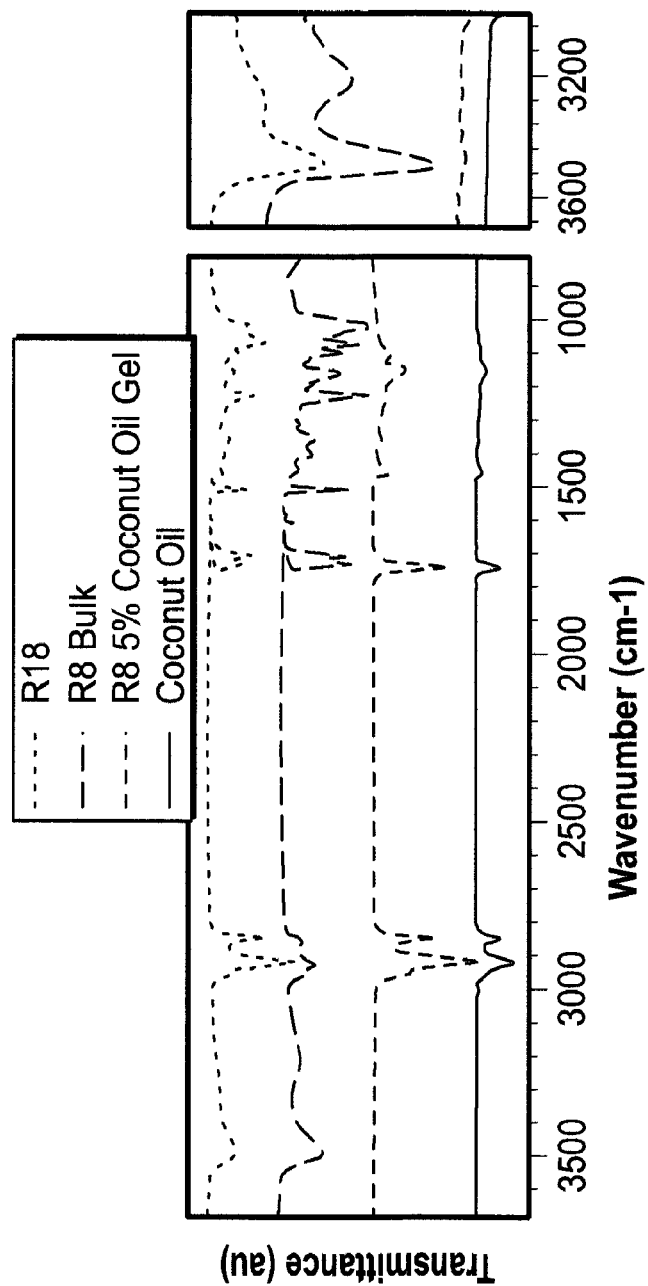
FIG. 3 is an FTIR Spectra of oleogel and bulk gelator samples (left) and the hydrogen-bonding region (right) displays weak O—H peaks in the gel spectrum comparable to those noted in oleogel samples.

Infrared Spectroscopy. The infrared spectroscopic characterization of neat oils, gelators, and composite gels highlighted the role of hydrogen bonding interactions in the gels. Characteristic of the oils, gelators, and oleogels are the strong saturated fatty acid carbonyl stretch at 1740 $cm^{-1}$. Oils, gelators, and the composite oleogels present intense methylene stretches at 2918 and 2850 $cm^{-1}$, which dwarf the methyl stretch at 2955 $cm^{-1}$ as the fatty acid chain length increases. See FIG. 3. Present in both the gelator and gel samples, and expectedly absent in the oil sample were broad O—H absorptions indicating intermolecular hydrogen bonding. Of the two broad O—H stretches in RKG8 and RKG18, samples gelator sample at 3500 and 3200 $cm^{-1}$ only the higher frequency peak appears as a weak and broad band in the oleogel spectrum (FIG. 3, right). Absorbing between 3504 and 3442 $cm^{-1}$, the oleogel's O—H stretch indicated the presence of hydrogen bonding in the gel network similar to those in the bulk form. Intermolecular hydrogen bonds, along with dispersive van der Waals forces serve to stabilize the solid crystalline network dispersed throughout the oil. This corresponds with the gelator's solubility in polar protic solvents; the intermolecular solvent-gelator hydrogen bonding disrupts gelator-gelator interactions preventing network formation. Indicative of increased hydrogen bonding and weakened O—H bonds are a decrease in the absorption frequency relating to increased inductive effects. In addition to the shift between the gel and its components, comparing the two neat RKG8 and RKG18 gelator's hydrogen bonding peaks, respectively 3493 and 3206 $cm^{-1}$, and 3489 and 3247 $cm^{-1}$ indicates subtle changes in the intermolecular hydrogen bonding. The difference between RKG8 and RKG18's FTIR spectrum indicates the ability to tailor the gel's intermolecular hydrogen bonding forces by varying gelator structure, but not necessarily adding or removing hydrogen bonding functional groups, instead affecting intermolecular interactions by merely changing saturated fatty acid chain length.

Figure 4:
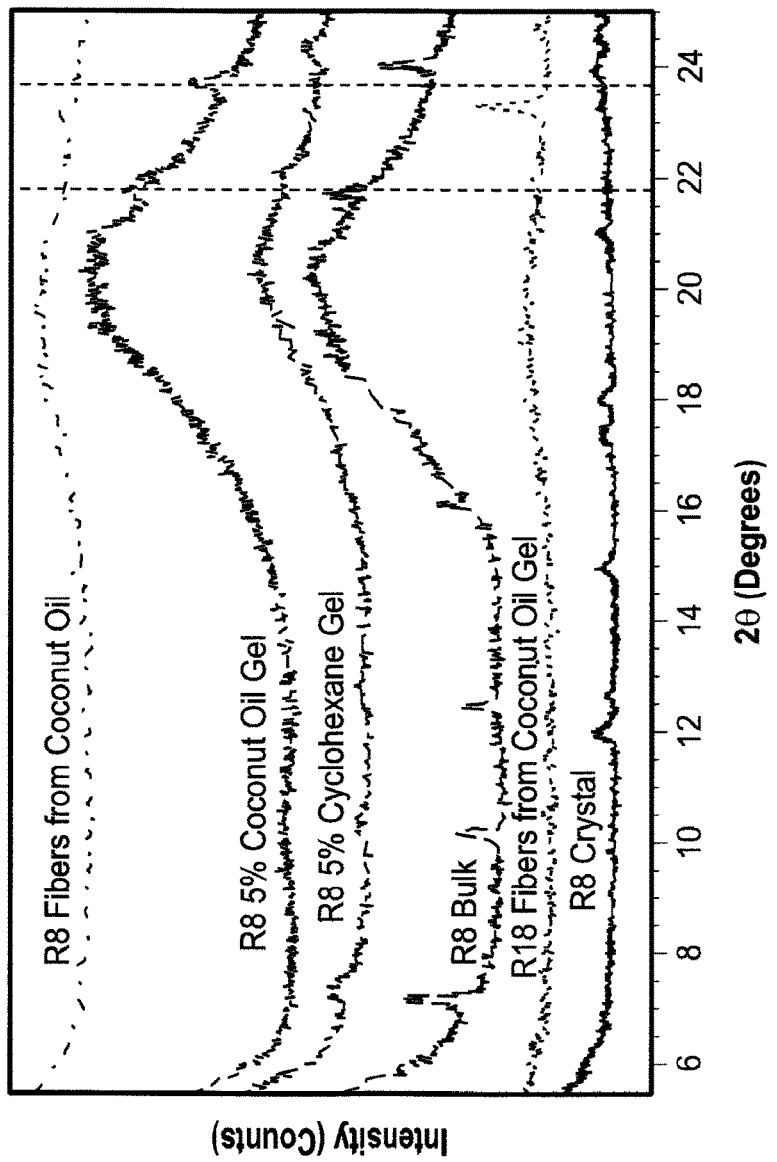
FIG. 4 is an XRD spectra of gelators and gels where dotted lines highlight location of peaks indicative of β' crystal polymorph.

Powder X-Ray Diffraction Analysis. By examining peak location of the bulk gelator, neat gels, and extracted fibers from gel samples, it is possible to classify the structure of the gel network. Small angle powder diffraction (1-10°) probes nanometer length longitudinal molecular packing, indicative in lipidic systems of bilayer thickness. Wide angle powder diffraction (5-45°) reveals information on crystal polymorphs, short-range structuring, and the maximum intermolecular distance. Polymorphs of the RKG8 gelator from clear crystal samples grown in water-acetone mixtures, and opaque bulk gelator precipitated from methanol exhibit distinctive curves. See FIG. 4. While all self-assembled gels and extracted fibers diffract at short angles indicating spacings of 2.98±0.02 nm, crystal samples display another long range peak at 3.30 nm, indicating multidimensional long range crystal growth compared to the single-dimension growth specific to self-assembled systems. Neat samples of the oils and fats absorbed broadly between 15 and 25°, as did the bulk RKG8 and RKG18 gelators, indicative of short-range ordering.

Between RKG8 and RKG18 spectra, the expected increase in the longitudinal spacing of 11 Å corresponds to the increase in chain length between caprylic and stearic acid. In comparing oleogel samples to structured oils and fats, it is possible to classify the gel network's polymorphic phase.

Typified by strong peaks at 4.2 and 3.8 Å, a β' conformation of the gelled lipidic amphiphiles indicates a kinetically controlled metastable structure compared to more and less stable forms, β and α respectively. Similar to lamellar arrangements of glyceride systems, a β' classification combined with the longitudinal spacing, indicates a collection of angled amphiphiles stacking to form a bilayer structure. This indicates that the gelators pack in a manner similar to natural fats structuring the oils like a fat mimic. This may represent the first step in creating oil-structuring agents with desirable mouthfeel or texture, as polymorphs may dissolve differently and influence taste.

Due to the relatively low signal given by the dispersed gel network, much work was done on neat gel structures from air dried gels, xerogels, and extracted gel fibers. Unlike volatile solvent samples, which may be easily lyophilized, oil samples must be extracted into compatible organic solvents leaving behind the gel network. Extracting clear oleogels with hexanes yields a solution of self-assembled structures with peaks corresponding to those found in the bulk gelator sample, such being artifacts of precipitation. Compared to the oleogel samples, extracted fibers diffracted at slightly higher 2θ values, indicating a more compact bilayer structure. Hexanes, a non-polar mixture of structural isomers may serve to form compact bulk structures due to hydrophobic effects with the glucoside's secondary hydroxyl groups. The resultant fibers lack the 4.2 Å diffraction peak, indicating a change in conformation of assembly, perhaps to a more compact polymorph (Table 3).

TABLE 3

XRD Peak values for Gelator Polymorphs

| XRD | Small Angle | | Wide Angle |
|---|---|---|---|
| Gelator | Angle (2θ) | Distance (Å) | Peaks (Å) |
| RKG8 Crystal | 3.30 | 26.7 | 7.41, 5.90, 5.11, 4.23, 3.71, 3.53, 2.96 |
| RKG8 Bulk | 2.99 | 29.6 | 7.10, 5.94, 5.16, 4.39, 3.74, 3.64, 3.54, 2.96 |
| RKG8 Fibres | 2.99 | 29.6 | 7.08, 5.93, 4.24, 3.83, 3.73 |
| RKG18 Fibres | 2.17 | 40.8 | 8.38, 7.65, 6.67, 6.52, 3.82, 3.60, 3.47 |

Figure 5:
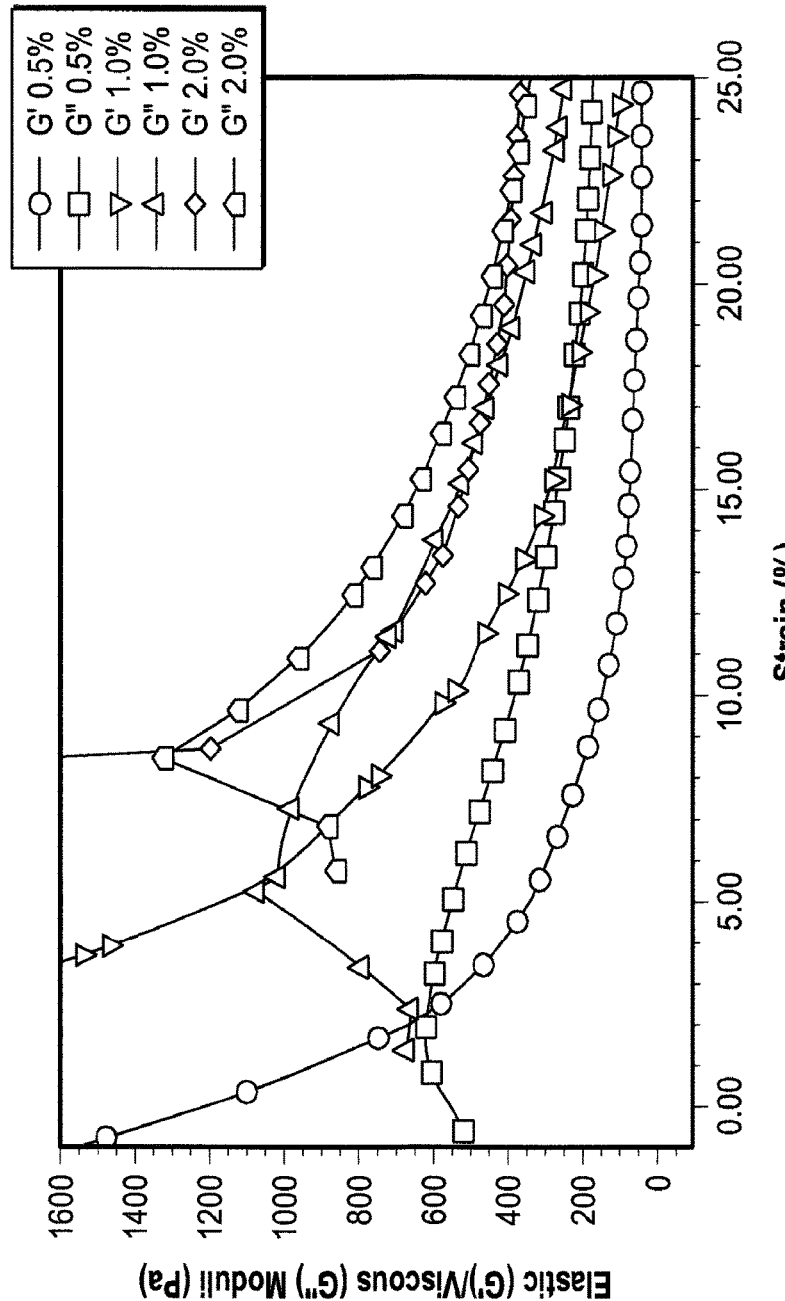
FIG. 5 displays oscillatory rheometry of coconut oleogels with a strain sweep curve of various coconut oleogel concentrations to highlight the effect of concentration on gel strength.
Figure 6:
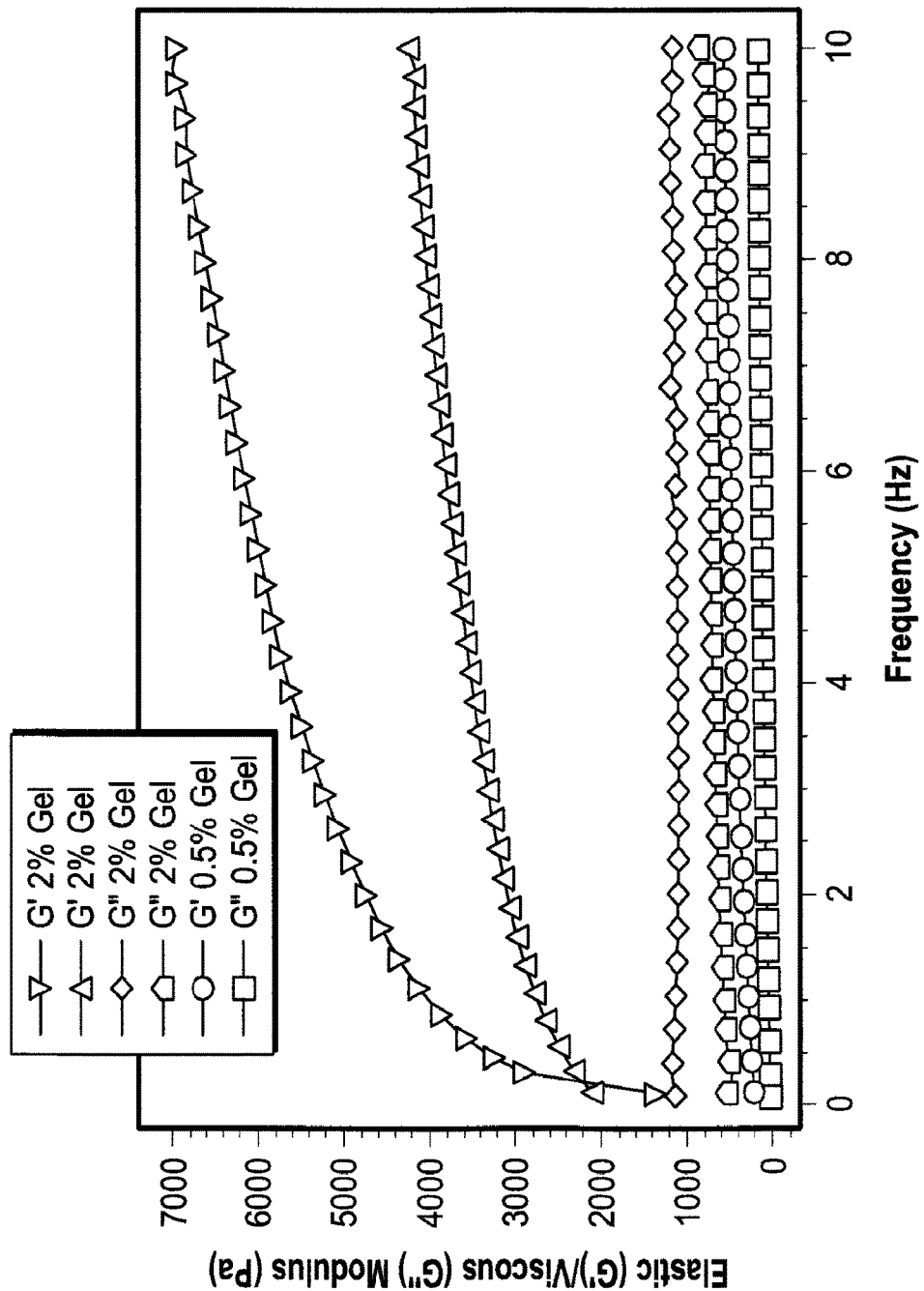
FIG. 6 displays oscillatory rheometry of coconut oleogels with a frequency sweet in the linear viscoelastic region of the same oleogels indicating the gelatinous nature of the binary mixtures.

Effect of Concentration and Oil type on Mechanical Gel Properties. Oscillatory rheometry elucidated an expected increase in gel strength corresponding to an increase in gelator concentration. Though it has been demonstrated that the gel point does not always correspond with the crossover point of the elastic and viscous moduli, which more accurately represents the beginning of stochastic nucleation, oscillatory strain sweep rheometry of the coconut oil gels demonstrates a marked increase in the position (% strain) of the crossover point corresponding to an increased gel concentration (FIG. 5). This indicates that the concentrated gels require greater deformations to disrupt the gel network than more dilute gels. It can also been seen that the storage modulus increases with an increase in gel concentration indicating the elastic and stability properties of the gel depend of the concentration of the gel (FIG. 6).

The storage moduli of coconut oil gels are seen to scale as a function of frequency. To examine the firmness or tolerance of the gel to external forces, a frequency sweep was conducted within the linear viscoelastic region. Indicating that the samples remain in a gel state, the larger magnitude of the storage modulus was seen to increase with an increase in frequency, while the viscous moduli remained relatively unchanged (FIG. 6). Indicative of junction zones between fibers in the gel network, the relatively unscaled curves for the dilute gels indicate fewer junction nodes. Their gel network therefore has fewer entangled nanostructures.

Gel Stability and Shelf Life. As the gelator molecules self-assemble to form a crystalline network, the cooling rate of the gel can greatly affect the microstructure of this self-assembly. By controlling the cooling rate as the mixture transitions from sol to gel, the crystalline architecture may be controlled. It has been previously demonstrated that slower cooling rates favor epitaxial growth, which leads to a finer monodisperse crystalline system. Particular to the coconut gel samples, the gel phase is comprised of two distinct phases: a clear gel and a white opaque gel, which are separated by a broad melting point (22-27° C.). In the transparent gels, coconut oil triglycerides crystallize trapped within the gel network, and blooms to form an opaque structure below room temperature. This thermoreversible coconut oil crystallization is kinetically delayed compared to neat oil samples, which become translucent, but remain liquid for hours at room temperature. While long chain oleate and stearate derivatives only formed translucent gels, the clear transparent coconut oil gels at low concentrations (about 0.5%) were stable over long periods at room temperature (greater than 6 months). Gels with higher gelator concentration (2.5-5 wt. %) were stored at an elevated temperature and displayed a tendency to aggregate to the air-gel interface forming a solid sponge-like disc, while lower concentration gels (0.25-2.0 wt. %) remained stable.

Materials and Methods

Materials. Natural and refined vegetable oils were purchased from local supermarkets. Unrefined (pressed) coconut oil: (Keratech LTD, India, and Brad's Organic Raw Oil, USA), refined: coconut oil (Bedesse Imports, USA), palm kernel oil (Dr. Adorable Inc., Ghana), hazelnut and grape seed oil (Trader Joe's, USA). Raspberry ketone glucoside was provided by Beijing Brilliance Bio, and fatty acid, methyl, and vinyl esters were purchased from TCI America. Lipase acrylic resin (Novozymes 435) from *Candida antarctica* (greater than or equal to 5,000 U/g), recombinant, expressed in *Aspergillus niger* was provided by Novozymes. Silica Gel (200-300 Mesh), hexanes, ethyl acetate and acetone were purchased from Thermo fisher (NY, N.Y.). Prior to use as solvent for reactions, acetone was distilled over calcium chloride.

Raspberry Ketone Glucoside Fatty Acid Ester Synthesis. In a 500 mL screw-cap Erlenmeyer flask, solid Novozymes 435 lipase catalyst (0.3 g/mmol glucoside) were added to mixture of raspberry ketone glucoside (2.0 mmol, 0.652 g), and fatty acid, methyl ester, or fatty acid vinyl ester (3:1 mmol acyl donor/glucoside ratio) containing 50 mL dried acetone. The reaction proceeded in an orbital shaker at 250 rpm, at 50° C. The reaction was monitored by thin-layer chromatography (TLC) with an ethyl acetate eluent and visualized using 5% sulfuric acid solution in water and gentle heating. After 24 hours, the bottom glucoside spot ($R_f$=0.1) faded and a product spot appeared ($R_f$=0.4). Before the solution is allowed to cool to room temperature the enzymes were filtered out and rinsed with acetone until the washings show no further product on TLC before they are air dried and stored for reuse. Acetone was evaporated under vacuum from the filtrate leaving behind a crude solid mixture of glucoside-ester product (% yield by acyl donor: methyl caprylate 87%, and 95% vinyl caprylate), unreacted acyl donor ($R_f$=0.8) when run with methyl or vinyl esters, and free fatty acid ($R_f$=0.7). The solid mixture was triturated thrice with 50 mL hexanes at 50° C. to remove the excess fatty acid and derivatives from the opaque light yellow bulk solid. For stearic and oleic acid derivatives the hexane-product mixture was centrifuged in a falcon tube at 3000 rpm for five minutes before decantation to avoid loss of suspended product. To remove trace elements of unreacted sugar, ester or acids the product (0.85 g) was dissolved in 25 mL methanol, and coated by evaporation onto 5.0 grams of silica gel before being spread onto a short silica plug (40.0 grams). The column was twice eluted to dryness with 200 mL ethyl acetate and the solvent was evaporated from the second fraction via rotary evaporation to afford the pure fatty acid glucoside ester product. Pure glucoside ester was dissolved in deuterated solvent (20 mg in 1 mL DMSO-$d_6$, toluene-$d_8$ or $CDCl_3$) and the solution was filtered through glass wool before recording a spectrum on a 300 MHz Bruker NMR Spectrometer.

Preparation and Characterization Molecular Gels. Gels were prepared by adding the solid glassy glycosides (10.0-50.0 mg gelator) to the desired solvent (1 mL). The mixture was then heated to disperse the gelator at five degrees below the boiling point of organic solvents, and at 125° C. for oils to produce a homogeneous sol. The sol was kept at this temperature for 10 minutes under constant agitation to fully disperse the gelator. The sol was then cooled to room temperature to allow for self-assembly and after a length of time (between 2-24 hours), the samples were inverted to confirm gel formation. The efficacy of gel formation was examined by determining the minimum gelation concentration (MGC) and gel-to-sol transition temperature ($T_{gel}$). Gel samples were diluted with solvent until after setting and vial inversion a gel, partial gel, or sol was formed. The gel transition temperature was determined by submersing a gel sample in an oil bath, and increasing the temperature until the gel flowed like a liquid, indicating the disassembly of the gelator structure. MGC was determined beginning from 5 wt. % samples (50 mg gelator in 1 mL solvent) or below the concentration of precipitation for gelators and diluting the samples until a sol is formed.

FT-IR Spectroscopic Characterization. The infrared spectra (FT-IR) of the neat bulk gelators and gel samples were measured using a Thermo Scientific Nicolet iS 10 FT-IR Spectrometer with an ATR configuration in the range of 600-4000 $cm^{-1}$.

Optical and Electron Microscopy. To study the self-assembled gel structures, microscopic samples of oleogels were prepared via multiple methods. For gels from volatile organic solvents the solvent was removed by evaporation at ambient pressure and temperature, under vacuum, and in liquid nitrogen by lyophilization. For oil samples the gel network was extracted using hexanes (50:1 v solvent: v oil) to remove the oil. The gel structures were subsequently dried under vacuum for 24 hours. Each of the samples was coated with a thin layer of carbon before recording images using a Zeiss Supra 55 Field Emission Scanning Electron Microscope. For polarized light microscopy samples were gelled on microscope slides with a lam, and imaged using a hot stage and Leica Microscope (DFC280) to investigate the gelation process.

Rheological Characterization of Gels. Oscillatory rheological measurements were performed on a stress-controlled rheometer (AR 2000 ex) with a cone and plate geometry (1° 58' 47" angle and 40 mm diameter with a truncation gap of 45 μm). 1 mL of gel was loaded onto the plate, and the cone was lowered to minimize the truncation gap. Precautions were taken to minimize shear-induced disruption of the gel network: before experiments samples were equilibrated within the geometry for 10 minutes. Excess gel was trimmed away from the cone to ensure optimal filling. Yield strain ($\sigma_y$) was examined for coconut oil gels (0.5, 1.0 and 2.0% caprylate gels in coconut oil) by performing oscillatory strain sweep measurements from 0.01 to 100% deformation at a fixed frequency of 1 Hz. Oscillatory frequency sweep measurements were performed in the frequency domain of 0.01-10 Hz, with a constant strain of 0.1%, which is within the determined linear viscoelastic regime of the samples. Experiments were run at 30° C., above the melting point of coconut oil, and repeated twice for each concentration.

X-Ray Diffraction. To elucidate the packing of the gelator molecules, some of the gel's fibers were isolated from oleogel samples via a similar extraction method described above. For bulk gelator samples the gelator was ground to a fine powder and spread over a clean glass slide before examination. Gel samples were prepared by forming the gel directly on the slide. Crystal samples were recrystallized from 1:1 acetone water mixtures by slow evaporation of the organic phase. Samples were recorded onto a PANalytical X'Pert Pro Powder Diffraction X-Ray Diffractometer. The instrument was operated under a voltage of 40 kV, a current of 40 mA, a 1/4° incident slit width and Cu $K_\alpha$ X-rays, (λ=1.54 Å). Small (1-10°) and wide (5-45°) angle X-ray diffractograms were recorded for samples at 25° C. The raw data was processed using the X'Pert High Score Plus software.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A gel comprising a hydrophobic liquid that has been formed into a gel through the addition of a composition having a structure given by:

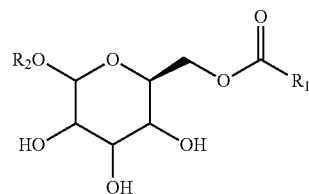

wherein

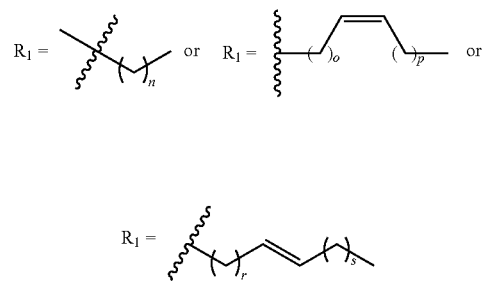

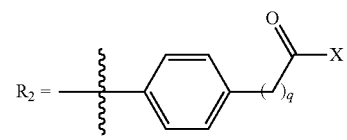

where n is an integer between 4 and 20; r and s are integers between 0 and 20 that sum to a digit between 4 and 20 and o and p are integers between 0 and 20 that sum to a number between 4 and 20;

$R_2$ is

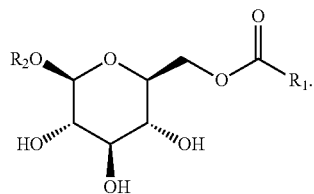

where q is an integer between 1 and 5 and X is a methyl, a hydroxyl or an ester.

2. The gel as recited in claim 1, wherein there is less than 2 grams of the composition per 100 grams of the hydrophobic liquid.

3. The gel as recited in claim 1, wherein the hydrophobic liquid is selected from the group consisting of coconut oil, palm kernel oil, hazelnut oil, grape seed oil, red palm oil and jojoba oil, olive oil, canola oil, soy oil, sunflower oil.

4. The gel as recited in claim 1, wherein the hydrophobic liquid is selected from the group consisting of hexanes, mineral oil, toluene and ether.

5. The gel as recited in claim 1, wherein the composition provides stereochemistry such that the structure is given by:

6. The gel as recited in claim 1, wherein the composition provides stereochemistry such that the structure is given by:

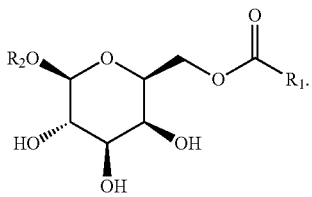

7. The gel as recited in claim 1, wherein the composition provides stereochemistry such that the structure is given by:

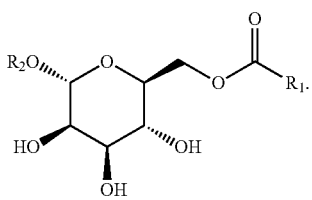

8. The gel as recited in claim 1, wherein $R_1$ is

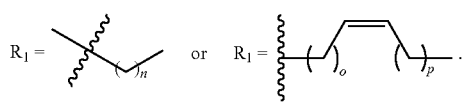

9. A gel comprising a hydrophobic liquid that has been formed into a gel through the addition of a composition having a structure given by:

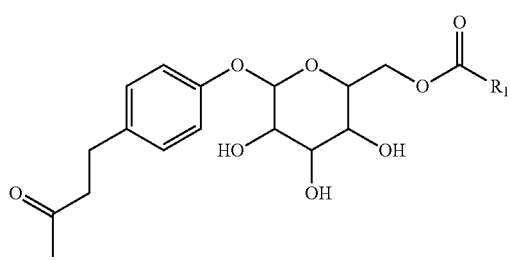

wherein

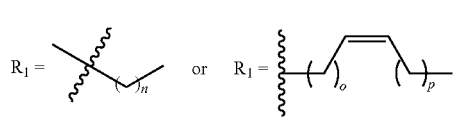

where n is an integer between 4 and 20 and o and p are integers that sum to a number between 4 and 20.

10. A method for forming a gel, the method comprising steps of:
exposing a hydrophobic liquid to a composition having a structure given by:

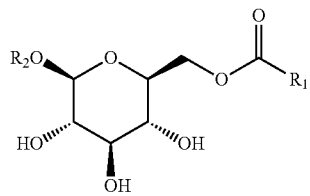

wherein

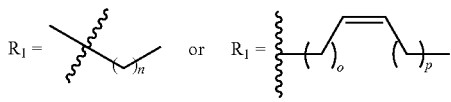

where n is an integer between 4 and 20 and o and p are integers that sum to a number between 4 and 20;
$R_2$ is

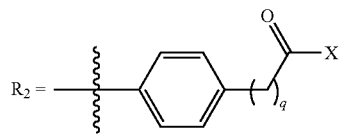

where q is an integer between 1 and 5 and X is a methyl, a hydroxyl or an ester;
permitting the hydrophobic liquid to thicken to form a gel.

11. The method as recited in claim 10, wherein q is 2 and X is methyl such that

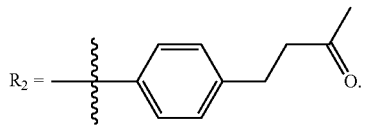

12. The method as recited in claim 11, wherein

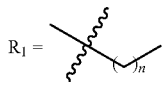

and n is between 5 and 8.

13. The method as recited in claim 11, wherein

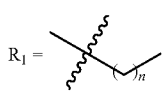

and n is 6.

14. The method as recited in claim 11, wherein

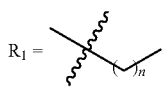

and n is between 15 and 20.

15. The method as recited in claim 11, wherein

and n is 18.

16. The method as recited in claim 11, wherein

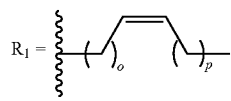

and o+p is between 15 and 18.

17. The method as recited in claim 11, wherein

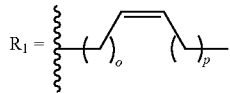

and o=p=7.

18. The method as recited in claim 10, wherein less than 2 grams of the composition per 100 grams of the hydrophobic liquid is used to effect the step of permitting the hydrophobic liquid to thicken.

19. The method as recited in claim 10, wherein the hydrophobic liquid is selected from the group consisting of coconut oil, palm kernel oil, hazelnut oil, grape seed oil, red palm oil, jojoba oil, olive oil, canola oil, soy oil and sunflower oil.

20. The method as recited in claim 10, wherein the hydrophobic liquid is selected from the group consisting of hexanes, mineral oil and toluene.

* * * * *